(12) United States Patent
Dhainaut et al.

(10) Patent No.: US 8,790,881 B2
(45) Date of Patent: Jul. 29, 2014

(54) METHOD FOR MEASURING IGG-MEDIATED COMPLEMENT ACTIVATION

(75) Inventors: Frederic Dhainaut, Boissy le Sec (FR); Gerald Perret, Choisy le Roi (FR)

(73) Assignee: Laboratoire francais du Fractionnement et des Biotechnologies, Les Ulis (FR)

( * ) Notice: Subject to any disclaimer, the term of this patent is extended or adjusted under 35 U.S.C. 154(b) by 0 days.

(21) Appl. No.: 13/695,820

(22) PCT Filed: May 4, 2011

(86) PCT No.: PCT/FR2011/051012
§ 371 (c)(1),
(2), (4) Date: Nov. 2, 2012

(87) PCT Pub. No.: WO2011/138561
PCT Pub. Date: Nov. 10, 2011

(65) Prior Publication Data
US 2013/0052659 A1 Feb. 28, 2013

(30) Foreign Application Priority Data
May 5, 2010 (FR) .................................. 10 53515

(51) Int. Cl.
*G01N 33/68* (2006.01)
*G01N 33/53* (2006.01)

(52) U.S. Cl.
USPC ............................................ 435/7.1; 435/7.4

(58) Field of Classification Search
CPC combination set(s) only.
See application file for complete search history.

(56) References Cited

U.S. PATENT DOCUMENTS

| | | | |
|---|---|---|---|
| 5,612,033 A | 3/1997 | Tsay et al. | |
| 5,972,632 A | 10/1999 | Tsay et al. | |
| 8,153,382 B2 * | 4/2012 | Chtourou et al. | 435/7.1 |

FOREIGN PATENT DOCUMENTS

| | | |
|---|---|---|
| WO | 2007/077365 | 7/2007 |
| WO | WO2011/131787 | * 10/2011 |

OTHER PUBLICATIONS

Meri et al., (Annals of the Rheumatic Diseases 1988; vol. 47, pp. 210-214).*
Sigma Product Information (2003, retrieved from URL www.sigmaaldrich.com/etc/medialib/docs/Sigma/Product_Information_Sheet/2/I3880pis.Par.0001.File.tmp/I3880pis.pdf).*
International Search Report dated Jul. 1, 2011, corresponding to PCT/FR2011/051012.
Spycher, et al.; In Vitro Comparison of the Complement-Scavenging Capacity of Different Intravenous Immunoglobulin Preparations; vol. 97, No. 4, 2009; pp. 348-354.
Leon, et al.; "Anticomplementary Activity of Equine Whole IgG Antivenoms: Comparison of three Fractionation Protocols"; vol. 45, No. 2; Jan. 1, 2005; pp. 123-128.
Buchacher, et al.; Anticomplementary Activity of IVIG Concentrates—Important Assay Parameters and Impact of IgG Polymers; vol. 98, No. 3; Apr. 2010; pp. E209-E218.
Kapp, et al.; "Detection of Complement Activation in Human Serum Using Complement C-5A-Induced Chemiluminescence of Human Granulocytes"; vol. 278, No. 1, 1985, pp. 41-43.
Ramasamy, et al.; "Measurement of Anticomplementary Activity in Therapeutic Intravenous Immunoglobulin Preparations"; vol. 25, No. 1, 1997, pp. 87-92.

* cited by examiner

*Primary Examiner* — Shafiqul Haq
*Assistant Examiner* — Carmencita M Belei
(74) *Attorney, Agent, or Firm* — Young & Thompson

(57) ABSTRACT

A method for measuring immunoglobulin G-mediated complement activation, includes the following steps:
a) preparing a sample A of immunoglobulin G and a sample B including natural serum, the natural serum optionally being diluted in a dilution buffer;
b) mixing sample A with sample B at a ratio (amount of IgG in A in grams):(volume of natural serum in B in liters) of between and 75, at a temperature of between 2° C. and 6° C., and subsequently incubating the resulting reaction mixture at a temperature of between 35° C. and 40° C. for a period of between 30 minutes and 2 hours;
c) cooling the reaction mixture obtained at the end of step b) to a temperature of between 0° C. and 4° C. in the presence of EDTA; and
d) measuring the amount of C5a fragment in the cooled reaction mixture obtained in c).

18 Claims, 2 Drawing Sheets

METHOD FOR MEASURING IGG-MEDIATED COMPLEMENT ACTIVATION

FIELD OF THE INVENTION

The invention relates to a method for measuring complement activation mediated by immunoglobulin G (IgG), in particular human intravenous immunoglobulin G (IVIG). The method makes it possible to select the IVIG according to the effect thereof on complement.

BACKGROUD OF THE INVENTION

IVIG is a concentrate of nonaggregated immunoglobulin G prepared from a pool of human plasma. The function thereof is intact and the purity thereof is as high as possible (>99.9%).

IVIG modulates, via selective and often distinct molecular mechanisms, certain biological processes involved in the innate or acquired immune response. These processes include:
- functional blocking of Fc receptors of the reticuloendothelial system. This makes it possible in particular to treat peripheral autoimmune cytopenias, such as idiopathic thrombocytopenic purpura;
- neutralization of autoantibodies and inhibition of the production thereof. IVIGs in fact contain anti-idiotypic antibodies. Such a neutralizing or inhibitory activity has been demonstrated, for example, for autoantibodies against factor VIII, DNA, intrinsic factor, thyreoglobulin and ANCAs (Anti-Neutrophil Cytoplasmic Antibodies);
- modulation of the production of cytokines (including IL-1, -2, -3, -4, -5, -10, TNF-$\alpha$, and GM-CSF) and of antagonists thereof (such as IL-1 RA), the result of which is an anti-inflammatory activity;
- complement activation;
- or else activation or functional blocking of the Fas cell death receptor (CD95).

Today, IVIG administration has become a therapeutic procedure comprising very few risks or side effects (<1%). The latter are minor owing to the constant improvement in the quality of these products.

Most of the side effects which are minor and transient in nature occur in the first hour of infusion; they comprise myalgia, headaches, hot flushes, sense of oppression, back pain, nausea, vomiting, bronchospasms, or else a change in pulse and/or arterial blood pressure. They are probably the consequence of a certain amount of immunoglobulin aggregation, of the formation of antigen-antibody complexes and the activation of complement, or of sugars present in the IVIG for the purpose of preventing their aggregation. These side effects are generally arrested by decreasing the rate of infusion or by rapidly administering steroids or antihistamines or even sympathicomimetics.

However, in certain cases, acute renal failure and/or hemolytic anemia can occur. In extreme cases, an anaphylactic reaction can occur, particularly in patients with a serum IgA deficiency.

Reducing the albeit minor side effects of IVIG therefore remains a major preoccupation in the development of these molecules.

Various methods are currently available for evaluating these side effects, for example the ACA (anticomplementary activity) test of the European pharmacopea, also known as assay for anticomplementary activity of immunoglobulin; or else the Coombs test. The ACA test is complex and involves reagents that are difficult to standardize. Indeed, the anticomplementary activity (ACA) of the immunoglobulin is determined by incubation of a given amount of the immunoglobulin to be examined with a given amount of guinea pig complement, followed by titration of the remaining complement. The remaining complement is measured by lysis of sheep erythrocytes sensitized with rabbit antibodies.

As for the Coombs test, it makes it possible to verify the absence of immunoglobulin that combine to red blood cells and that can bring about red blood cell agglutination and lysis.

There is therefore a need to have tests which are sufficiently sensitive for selecting various qualities of IVIG, and which are easy to set up for routine use. There is also a need to have relevant and predictive tests for humans. These tests must in particular demonstrate good quality and sufficient safety of the IVIG for the patient.

SUMMARY OF THE INVENTION

Consequently, the applicant has endeavored to develop a novel in vitro method for evaluating the action of IgG, in particular of IVIG, on complement activation. This method makes it possible to easily select the IgG having the fewest possible side effects, with sufficient sensitivity for distinguishing between various qualities of IgG.

This method uses human serum and is, consequently, predictive of the result on humans.

The subject of the present invention is therefore a method for measuring immunoglobulin G-mediated complement activation, comprising the following steps:
a) preparing a sample A of immunoglobulin G (IgG) and a sample B comprising natural serum, said natural serum optionally being diluted in a dilution buffer;
b) mixing sample A with sample B at a ratio (amount of IgG in A in grams):(volume of natural serum in B in liters) of between 30 and 75, at a temperature of between 2° C. and 6° C., and subsequently incubating the resulting reaction mixture at a temperature of between 35° C. and 40° C. for a period of between 30 minutes and 2 hours;
c) cooling the reaction mixture obtained at the end of step b) to a temperature of between 0° C. and 4° C. in the presence of EDTA;
d) measuring the amount of C5a fragment in the cooled reaction mixture obtained in c).

Of course, the method according to the invention is an in vitro method.

This method measures complement activation mediated by IgG, preferably human IgG, preferably IVIG. Thus, preferably, sample A is a sample of IVIG.

Step a) of the method according to the invention comprises preparing a sample A of IgG. This sample A can in particular be obtained from commercial IVIG, such as Privigen from CSL Behring AG, Gamunex from Bayer Corporation, Intratect from Biottest Pharma GmbH, Kiovig from Baxter AG or Octagam from Octapharma. The preparation may be in liquid or lyophilized form, such as Sandoglobulin from CSL Behring AG.

Sample A can also be obtained from noncommercial IVIG, such as novel IVIG (IgNG). The IgG, preferably IVIG, can be diluted in a conventionally used buffer medium, such as phosphate buffered saline/bovine serum albumin (i.e. PBS-BSA). Preferably, the IgG, in particular the IVIG, is diluted in a buffer comprising BSA.

Step a) also comprises the preparation of a sample B comprising natural serum. The term "serum" is intended to mean blood plasma from which the fibrin has been removed. The term "natural serum" is intended to mean a nondiluted serum. The natural serum is preferably natural human serum.

The natural serum of sample B can originate from various donors, having various blood groups. Preferably, the natural serum is a human serum of blood group AB+.

Preferably, the natural serum is stored frozen until use, for example at a temperature of −80° C. At the time of use, it is then gently thawed to the mixing temperature.

Sample B may contain only natural serum; alternatively, sample B comprises natural serum diluted in a dilution buffer.

Such a dilution buffer is conventional, and can be chosen from phosphate buffered saline (PBS) and PBS-BSA.

Preferably, the dilution buffer comprises BSA; preferably, the dilution buffer is PBS-BSA.

Preferably, sample A comprises IgG diluted in a buffer identical to the dilution buffer for sample B.

Once samples A and B have been prepared, they are mixed and subsequently incubated under specific conditions during step b) of the method according to the invention.

Indeed, the mixing of samples A and B is carried out:

at a ratio (amount of IgG in A in grams):(volume of natural serum in B in liters) of between 30 and 75, and at a temperature of between 2° C. and 6° C.

The ratio (amount of IgG in A in grams):(volume of natural serum in B in liters) defines the amount of IgG which acts on a volume of natural serum. The amount of IgG present in A is determined in grams, and the volume of natural serum present in B is determined in liters.

For example, if sample A corresponds to 20 μl of a solution of IgG at 100 g/l, then the amount of IgG present in A is $100 \times 20 \times 10^{-6} = 2 \times 10^{-3}$ g. Similarly, if sample B corresponds to 80 μl of a solution of natural serum diluted to 25% in a dilution buffer, then the volume of natural serum in B is $80 \times 10^{-6} \times 0.25 = 2 \times 10^{-5}$ l (i.e. 20 μl). In this case the ratio (amount of IgG in A in grams):(volume of natural serum in B in liters) is 2/0.02, i.e. 100.

Preferably, the ratio (amount of IgG in A in grams):(volume of natural serum in B in liters) is between 35 and 70, preferably between 40 and 65, preferably between 45 and 60, preferably between 45 and 55, preferably is approximately 50.

The mixing temperature is between 2° C. and 6° C., preferably between 3° C. and 5° C., preferably is approximately 4° C. The mixing can thus be carried out in a container, for example a test tube, stored in ice until incubation.

If several samples A and B must be tested, all the reaction mixtures are prepared at a temperature of between 2° C. and 6° C., preferably at 4° C., and the incubation is subsequently carried out simultaneously in a uniform manner.

Once the mixture of samples A and B has been obtained (hereinafter reaction mixture), the reaction mixture is incubated at a temperature of between 35° C. and 40° C. for a period of between 30 minutes and 2 hours. Preferably, the reaction mixture is incubated at a temperature of approximately 37° C., for a period of between 45 minutes and 1 h30, preferably between 45 minutes and 1 h, preferably approximately 1 h.

The incubation is carried out with standard equipment, for example in an incubator or in a thermostated water bath.

The reaction mixture is then cooled during a step c), in order to stop the biological reactions taking place during incubation. This cooling of the reaction mixture obtained at the end of step b) is carried out at a temperature of between 0° C. and 4° C. in the presence of EDTA. Step c) can thus take place by putting the test tubes comprising the incubated reaction mixtures in ice, and adding EDTA in a sufficient amount. Preferably, the EDTA is used at a concentration of between 50 mM and 200 mM, preferably of approximately 100 mM.

In the reaction medium obtained at the end of step c), the amount of C5a complement fragment is then measured (step d)).

Step d) can be carried out by any method of measurement conventionally used, and in particular using commercial kits. For example, it can be carried out by ELISA, using commercial kits for detecting the C5a protein, such as those sold by Quidel or R&D systems or Abcam.

The amount of C5a fragment released during the method according to the invention is determined for evaluating the possible side effects of the IgG tested. The higher this amount, the more adverse side effects the IgG will have.

In order to evaluate the amount of IgG as accurately and sensitively as possible, the method according to the invention advantageously comprises an additional step e) of comparing the amount obtained in d) (i.e. amount of C5a fragment released by virtue of sample A and therefore by virtue of the IgG tested) with the amount obtained by replacing sample A with a positive control.

The term "positive control" is intended to mean a sample responsible for maximum complement activation, and therefore for maximum release of C5a fragment. This positive control thus serves as a reference, since it corresponds to 100% complement activation.

The positive control is advantageously chosen from samples of lipopolysaccharides (LPS), and in particular from the LPS *Escherichia coli* (*E. coli*) serotype 0127:B8 purified by ion exchange chromatography, the LPS of *E. coli* serotype K-235, the LPS of *Salmonella enterica* serotype typhimurium, the LPS of *Klebsiella pneumoniae*, the LPS of *E. coli* serotype 0127:B8, extracted with trichloroacetic acid, the LPS of *Shigella flexneri* mutants, and the LPS of *E. coli* serotype 0127:B8, purified by extraction with phenol.

Preferably, the positive control is made up of the LPS of *E. coli* serotype 0127:B8, purified by extraction with phenol. These LPS in fact strongly activate C5a fragment release, reproducibly.

Preferably, the method according to the invention also comprises an additional step f) of comparing the amount obtained in d) (i.e. amount of C5a fragment released by virtue of sample A and therefore by virtue of the IgG tested) with the amount obtained by replacing sample A with a negative control. The term "negative control" is intended to mean a sample responsible for the release of a basal amount of C5a fragment. This negative control corresponds in particular to a sample comprising only the dilution buffer for sample B, for example the PBS buffer or the PBS-BSA buffer.

This step f) can be carried out at the same time as, before or after step e).

Preferably, the method according to the invention comprises, like step e) above, a step of measuring the percentage complement activation, obtained by means of the following formula:

$$[\text{test}-\text{negative control}]/[\text{maximum complement activation}-\text{negative control}] \times 100$$

in which:

"test" is the amount of C5a fragment measured in the reaction mixture tested;

"negative control" is the amount of C5a fragment measured in the reaction mixture in which sample A is replaced with the dilution buffer;

"maximum complement activation" is the amount of C5a fragment measured in the reaction mixture in which sample A is replaced with LPS of *E. coli* serotype 0127:B8, purified by extraction with phenol.

Preferably, when a positive control made up of LPS, in particular the LPS of E. coli serotype 0127:B8, purified by extraction with phenol is used, the ratio (amount of LPS in grams):(volume of natural serum in B in liters) is between 6 and 15, preferably between 7 and 14, preferably between 8 and 13, preferably the ratio is approximately 10.

DETAILED DESCRIPTION OF THE INVENTION

The following examples illustrate the invention without, however, limiting the scope thereof.

EXAMPLE 1

General Method for Measuring IgG-Mediated Complement Activation

Material:

Natural human serum: obtained by mixing the natural serum of four donors of type AB, and stored at −80° C. The serum is carefully thawed at 4° C. before use.

For the ELISA assay, the anti-human-C5a monoclonal antibodies (for the coating) and the biotinylated anti-human-C5a polyclonal antibodies (for the visualizing) come from R&D systems.

C5a Release Test:

Step a): preparation of 20 μl of IgG tested at 50 mg/ml in a PBS-1% BSA buffer (sample A) and of 80 μl of natural human serum diluted to 25% in PBS-1% BSA (sample B).

Step b): mixing of sample A with sample B. All the mixture tubes are kept in a water/ice mixture until incubation.

For each sample, five independent C5a activation tests are carried out:

The maximum complement activation (positive control) is obtained by replacing sample A comprising the IgG tested with LPS of E. coli serotype 0127:B8 purified by extraction with phenol (10 mg/ml);

A negative control is carried out with only PBS-BSA buffer.

The mixtures are incubated for 1 h at 37° C.

Step c): the reactions are stopped by placing the tubes in ice and adding 1 μl of 100 mM of EDTA.

Step d): after incubation and cooling, the release of the C5a fragment is measured in triplicate for each tube by means of an ELISA assay:

Dilution of each mixture: 1/50 in PBS/1% BSA

Coating antibody: 0.4 μg/ml–100 μl/Visualizing antibody: 100 ng/ml–100 μl.

The optical density is measured for each mixture using a microplate reader (Perkin) adapted to the visualizing system associated with the antibody. It may be a reader in the visible range in the case of conventional HRP-OPD visualization, or a fluorescence reader if the antibody is grafted with a fluorescent group.

Results: the percentage complement activation is obtained by means of the following formula:

[test−negative control]/[maximum complement activation−negative control]×100

For each mixture, the average obtained for the five independent tests and the standard deviation are measured.

EXAMPLE 2

Evaluation of the Maximum Complement Activation by Various LPSs

The protocol of example 1 is used to measure the maximum complement activation by the various LPSs which follow:

LPS A: LPS of E. coli serotype 0127:B8, purified by ion exchange chromatography

LPS B: LPS of E. coli serotype K-235

LPS C: LPS of Salmonella enterica serotype typhimurium

LPS D: LPS of Klebsiella pneumoniae

LPS E: LPS of E. coli serotype 0127:B8, extracted with trichloroacetic acid

LPS F: LPS of Shigella flexneri mutant

Reference LPS: LPS of E. coli serotype 0127:B8, purified by extraction with phenol.

The amount of C5a fragment released is evaluated on days 1 to 5 for each mixture.

Figure 1:
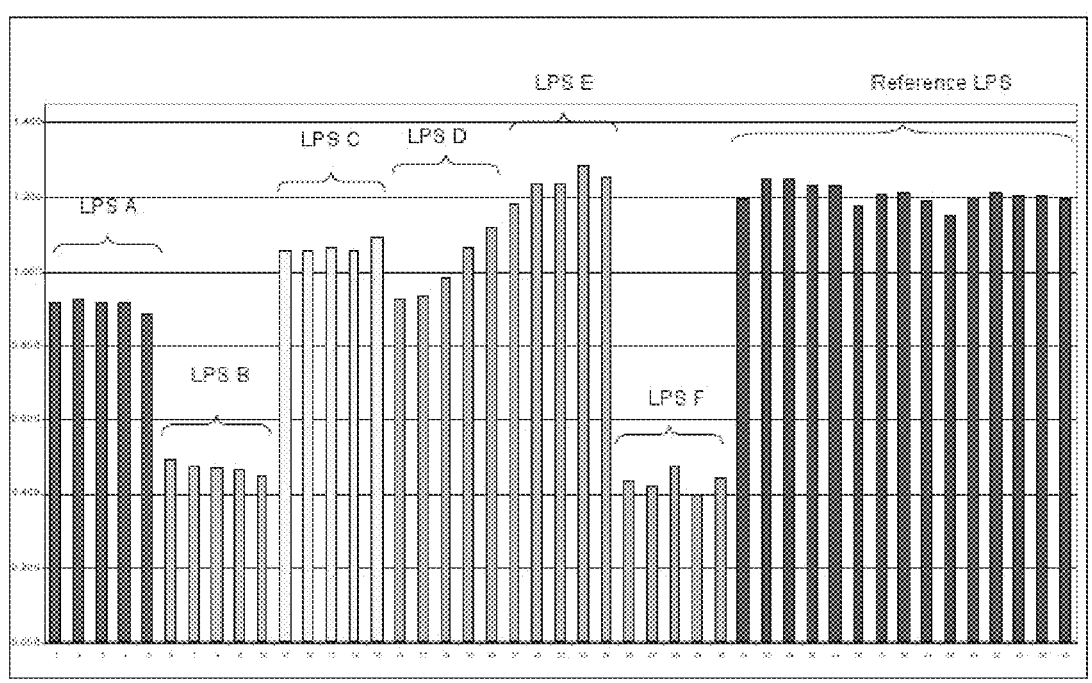
FIG. 1 illustrates the maximum complement activation by various LPSs.

The results are presented in FIG. 1. For each of LPS A to F, the optical densities (ODs) obtained on D1, D2, D3, D4 and D5 are successively represented.

For the reference LPS, the ODs obtained during each measurement for the five days are given successively (i.e. D1: 1st measurement, 2nd measurement and 3rd measurement of the triplicate; D2: 1st measurement, 2nd measurement and 3rd measurement of the triplicate etc., up to D5: 1st measurement, 2nd measurement and 3rd measurement of the triplicate).

The results demonstrate that the reference LPS is one of those which strongly activates C5a, in a constant manner over time.

EXAMPLE 3

Measurement of IVIG-Mediated Complement Activation

Protocol:

The protocol of example 1 is used to measure the percentage activation of an IgNG and of various commercial IVIGs.

The IgNG (ClairYg) is obtained according to the method developed by the applicant in example 1 of international patent application WO 2007/077365. Four commercial liquid IVIGs are also tested, which are:

IVIG1—OCTAGAM® sold by Octapharma;

IVIG2—GAMMAGARD® sold by Baxter;

IVIG3—GAMUNEX® sold by Talecris;

IVIG4—PRIVIGEN® sold by CSL Behring.

For the ELISA assay, microwell plates are coated with 100 μl of anti-C5a antibody at 0.4 μg/ml in a buffer comprising 0.1 M carbonate, pH 9.6, overnight at 4° C. After saturation with PBS+1% BSA, the samples and controls are diluted in the saturation buffer, deposited on a plate and incubated for 2 h at 20° C. The biotinylated polyclonal antibody is then added and visualized with streptavidin coupled to a peroxydase. The absorbance at 492 nm is measured with an ELISA reader (Bio-Tek instrument). The Percentage Complement Activation is obtained according to the following formula:

[test−negative control]/[maximum complement activation−negative control]×100

For each sample, the result corresponds to the mean of the five independent activations.

Figure 2:
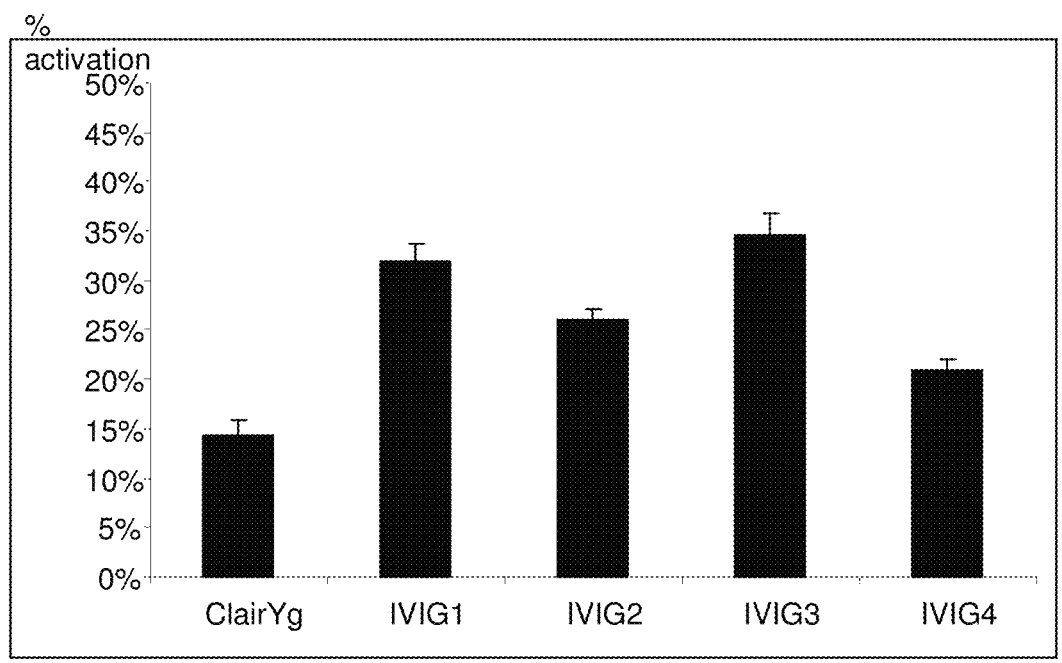
FIG. 2 illustrates the measurement of IVIG-mediated complement activation.

Results:

The results are given in FIG. 2.

It is clear that the percentage activation of C5a mediated by ClairYg is significantly the lowest (approximately 15%), which suggests, significantly, a better tolerance of this IVIG compared with the four commercial IVIGs.

The invention claimed is:

1. A method for measuring immunoglobulin G-mediated complement activation, comprising the following steps:
   a) preparing a sample A of immunoglobulin G (IgG) and a sample B comprising natural serum, said natural serum optionally being diluted in a dilution buffer;
   b) mixing sample A with sample B at a ratio (amount of IgG in sample A in grams):(volume of natural serum in sample B in liters) of between 30 and 75, at a temperature of between 2° C. and 6° C., and subsequently incubating the resulting reaction mixture at a temperature of between 35° C. and 40° C. for a period of between 30 minutes and 2 hours;
   c) cooling the reaction mixture obtained at the end of step b) to a temperature of between 0° C. and 4° C. in the presence of EDTA; and
   d) measuring the amount of C5a fragment in the cooled reaction mixture obtained in c).

2. The method according to claim 1, wherein the sample A:sample B ratio is between 35 and 70.

3. The method according to claim 1, wherein the reaction mixture is incubated in step b) at a temperature of approximately 37° C., for a period of between 45 minutes and 1 hour.

4. The method according to claim 1, wherein the EDTA in step c) is present at a concentration of between 50 mM and 200 mM.

5. The method according to claim 1, wherein sample A comprises intravenous immunoglobulin G (IVIG).

6. The method according to claim 1, wherein sample B comprises human serum of blood group AB+.

7. The method according to claim 1, further comprising
   e) comparing the amount of C5a fragment obtained in d) with the amount of C5a fragment obtained by the following process:
   a') preparing a sample of lipopolysaccharides (LPS) of *E. coli* serotype 0127:B8, purified by extraction with phenol, and a sample B comprising natural serum, said natural serum optionally being diluted in a dilution buffer;
   b') mixing the sample of LPS with sample B at a ratio (amount of LPS in grams):(volume of natural serum in B in liters) of between 30 and 75, at a temperature of between 2° C. and 6° C., and subsequently incubating the resulting reaction mixture at a temperature of between 35° C. and 40° C. for a period of between 30 minutes and 2 hours;
   c') cooling the reaction mixture obtained at the end of step b) to a temperature of between 0° C. and 4° C. in the presence of EDTA; and
   d') measuring the amount of C5a fragment in the cooled reaction mixture obtained in c).

8. The method according to claim 1, further comprising
   e) measuring the percentage complement activation, obtained by the following formula:

(test−negative control)/(maximum complement activation−negative control)×100 in which:
   "test" is the amount of C5a fragment measured in the reaction mixture tested;
   "negative control" is the amount of C5a fragment measured in the reaction mixture in which sample A is replaced with the dilution buffer;
   "maximum complement activation" is the amount of C5a fragment measured in the reaction mixture in the method according to claim 1 in which sample A is replaced with lipopolysaccharides (LPS) of *E. coli* serotype 0127:B8, purified by extraction with phenol.

9. The method according to claim 7, wherein the ratio (amount of LPS in grams):(volume of natural serum in sample B in liters) is between 6 and 15.

10. The method according to claim 1, wherein step d) is carried out by an ELISA assay.

11. The method according to claim 2, wherein the reaction mixture is incubated in step b) at a temperature of approximately 37° C., for a period of between 45 minutes and 1 hour.

12. The method according to claim 3, wherein sample A comprises intravenous immunoglobulin G (IVIG).

13. The method according to claim 3, sample B comprises human serum of blood group AB+.

14. The method according to claim 3, further comprising
   step e) of comparing the amount of C5a fragment obtained in d) with the amount of C5a fragment obtained by the following process:
   a') preparing a sample of lipopolysaccharides (LPS) of *E. coli* serotype 0127:B8, purified by extraction with phenol, and a sample B comprising natural serum, said natural serum optionally being diluted in a dilution buffer;
   b') mixing the sample of LPS with sample B at a ratio (amount of LPS in grams):(volume of natural serum in sample B in liters) of between 30 and 75, at a temperature of between 2° C. and 6° C., and subsequently incubating the resulting reaction mixture at a temperature of between 35° C. and 40° C. for a period of between 30 minutes and 2 hours;
   c') cooling the reaction mixture obtained at the end of step b) to a temperature of between 0° C. and 4° C. in the presence of EDTA; and
   d') measuring the amount of C5a fragment in the cooled reaction mixture obtained in c).

15. The method according to claim 3, further comprising step e) measuring the percentage complement activation, obtained by the following formula:

(test−negative control)/(maximum complement activation−negative control)×100 in which:
   "test" is the amount of C5a fragment measured in the reaction mixture tested;
   "negative control" is the amount of C5a fragment measured in the reaction mixture in which sample A is replaced with a dilution buffer;
   "maximum complement activation" is the amount of C5a fragment measured in the reaction mixture in the method according to claim 3 in which sample A is replaced with lipopolysaccharides (LPS) of *E. coli* serotype 0127:B8, purified by extraction with phenol.

16. The method according to claim 8, wherein the ratio (amount of LPS in grams):(volume of natural serum in sample B in liters) is between 6 and 15.

17. The method according to claim 1, wherein the sample A:sample B ratio is between 45 and 60.

18. The method according to claim 7, wherein the ratio (amount of LPS in grams):(volume of natural serum in sample B in liters) is between 8 and 13.

* * * * *